United States Patent [19]  
Ikariya et al.

[11] Patent Number: 4,699,994
[45] Date of Patent: Oct. 13, 1987

[54] METHOD OF MANUFACTURING DIPHENYLMETHANE DICARBAMIC ACID DIESTERS

[75] Inventors: Takao Ikariya, Tokyo; Masanori Itagaki, Yokohama; Masatsugu Mizuguchi, Kawasaki; Itaru Sakai, Yokohama; Osamu Tajima, Kamakura, all of Japan

[73] Assignee: Nippon Kokan Kabushiki Kaisha, Tokyo, Japan

[21] Appl. No.: 905,067

[22] Filed: Sep. 8, 1986

[30] Foreign Application Priority Data

Sep. 18, 1985 [JP] Japan .................. 60-204361

[51] Int. Cl.$^4$ ............... C07C 125/06; C07C 125/073
[52] U.S. Cl. ................................................. 560/025
[58] Field of Search .......................................... 560/25

[56] References Cited

FOREIGN PATENT DOCUMENTS 1120051 3/1982 Canada .

Primary Examiner—Werren B. Lone
Attorney, Agent, or Firm—Frishauf, Holtz, Goodman & Woodward

[57] ABSTRACT

According to a method of manufacturing a diphenylmethane dicarbamic acid ester by reacting an N-phenyl carbamic acid diester with a methylating agent in an aqueous acid solution, the aqueous acid solution is an aqueous inorganic acid solution, and the concentration of the N-phenyl carbamic acid ester in the aqueous acid solution is not more than the solubility thereof at the reaction temperature.

11 Claims, 1 Drawing Figure

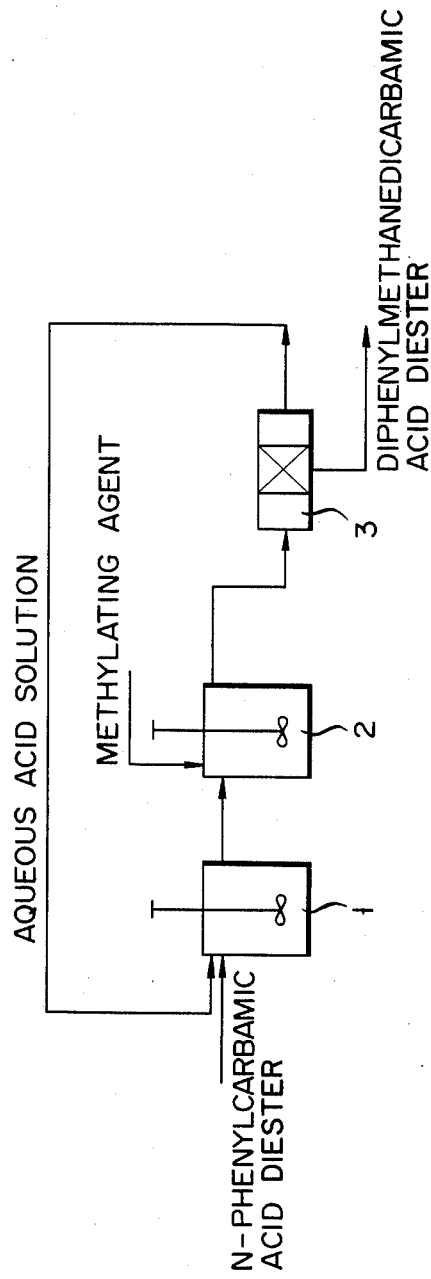

METHOD OF MANUFACTURING DIPHENYLMETHANE DICARBAMIC ACID DIESTERS

BACKGROUND OF THE INVENTION

1. Field of the Invention

The present invention relates to a method of manufacturing diphenylmethane dicarbamic acid diester by reacting an N-phenyl carbamic acid ester with a methylating agent in an aqueous acid solution.

2. Description of the Prior Art

Diphenylmethanediisocyanate (to be referred to as an MDI hereinafter) is a useful compound for use as a material for manufacturing high-quality polyurethane resin.

According to a conventional method of manufacturing the MDI on industrial basis, aniline is reacted with formaldehyde to prepare diaminodiphenylmethane, and the resultant diaminodiphenylmethane is reacted with toxic phosgene to prepare the MDI. In the reaction process with phosgene, a large amount of hydrochloric acid is produced and must be properly treated, thus posing a number of problems.

Another conventional method is proposed to prepare MDI. In this method, an N-phenyl carbamic acid ester is reacted wtih a methylating agent to obtain a diphenylmethane dicarbamic acid ester. The resultant ester is thermally decomposed, to prepare the MDI. In the initial condensation process of this method, in addition to the diphenylmethane dicarbamic acid ester as a binuclear compound, further condensed compounds such as trinuclear and tetranuclear compounds are simultaneously obtained. These oligomers are thermally decomposed to obtain so-called crude MDIs, i.e., polymethylene polyphenylisocyanates. However, these crude MDIs have a lower commercial value than that of a pure MDI prepared by thermally decomposing diphenylmethane dicarbamic acid diester. For this reason, demand has arisen for providing a method of preparing a diphenylmethane dicarbamic acid diester wtih high selectivity.

For example, in Japanese Patent Disclosure (Kokai) No. 55-81850, N-phenyl carbamic acid ester is reacted with an aqueous solution of formaldehyde in an aqueous solution of hydrochloric acid. According to this method, even if a reacfion is performed for a long period of time, a great amount of nonreacted materials is left and compounds having three or more nuclei are undesirably produced in a total amount of 20% or more. In this reaction system, the reaction progresses while an organic phase is suspended in an aqueous phase. The organic phase contains both phenyl carbamic acid ester as a starting material and diphenylmethane dicarbamic acid ester as a target product. These materials are further condensed to produce compounds having three or more nuclei. In such a reaction system, an aqueous solution of an acid can be easily separated from an organic layer, by layer separation. However, separation of a product, a nonreacted material, and a byproduct must be achieved by distillation.

In Japanese Patent Disclosure (Kokai) No. 55-57550, an organic acid such as trifluoromethane sulfonic acid and an organic solvent such as nitrobenzene are used to prepare a homogeneous reaction system. This reaction system has a high reaction rate, so that the condensation rate of diphenylmethane dicarbamic acid ester is also high. More specifically, diphenyl carbamic acid diester and diphenylmethane dicarbamic acid diester are present in the reaction chamber at an identical phase, so that compounds having three or more nuclei are also produced. In addition, according to this reaction system, an organic acid must be extracted with water and the desired compound must be separated by distillation, thus complicating the separation process. The acid cannot be reused, in practice.

SUMMARY OF THE INVENTION

It is an object of the present invention to provide a method of manufacturing diphenylmethane dicarbamic acid diester at a high selectivity ratio, by minimizing side reactions.

In order to achieve the above object of the present invention, a method is provided for manufacturing a diphenylmethane dicarbamic acid diester by reacting an N-phenyl carbamic acid diester with a methylating agent in an aqueous acid solution, wherein the aqueous acid solution is an aqueous inorganic acid solution, and the concentration of the N-phenyl carbamic acid ester in the aqueous acid solution is lower than the solubility thereof, at the reaction temperature.

BRIEF DESCRIPTION OF THE DRAWING

The drawing shows a reaction system according to an embodiment of the present invention.

DETAILED DESCRIPTION OF THE PREFERRED EMBODIMENT

According to the present invention, an N-phenyl carbamic acid ester is reacted with a methylating agent in an aqueous inorganic acid solution.

Preferred examples of the aqueous inorganic acid solution are an aqueous hydrochloric acid solution, an aqueous sulfuric acid solution, and an aqueous phosphoric acid solution. The ratio of solubility of the N-phenyl carbamic acid ester as a starting material to that of diphenylmethane dicarbamic acid diester as a product is 0.1 or less at the reaction temperature, when such an aqueous acid solution is used. The acid concentration is preferably 1 to 80% by weight for hte following reason: If the acid concentration is increased, the solubility of the acid in the solution of the N-phenyl carbamic acid ester as a material is increased, so that the material treatment capacity is increased. However, if the acid concentration is excessively increased, hydrolysis of the material tends to occur.

The N-phenyl carbamic acid ester used in the present invention is represented by general formula (I) below:

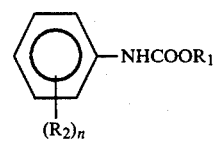

wherein $R_1$ is an alkyl group, an alicyclic group, or an aromatic group, $R_2$ is a hydrogen atom, an alkyl group, a halogen atom, a nitro group, or an alkoxy group, such a substituent being bonded to the urethane group at the o- or m- position, and n is an integer of 0 to 4. If n is 2 or more, each $R_2$ may be an identical atom or group, or a different atom or group from that of another $R_2$.

Examples of the N-phenyl carbamic acid ester are preferably N-phenyl carbamic acid methyl, N-phenyl carbamic acid ethyl, N-phenyl carbamic acid n-propyl, N-phenyl carbamic acid isopropyl, N-phenyl carbamic acid phenyl, N-phenyl carbamic acid cyclohexyl, N-o-chlorophenyl carbamic acid methyl, N-m-chlorophenyl carbamic acid methyl, N-o-methylphenyl carbamic acid methyl, N-m-methyl carbamic acid methyl, N-2,6-dimethyl carbamic acid methyl, N-o-nitrophenyl carbamic acid methyl, and N-o-methoxy carbamic acid methyl.

The concentration of an N-phenyl carbamic acid ester in the aqueous acid solution is less than its solubility at the reaction temperature. More specifically, although the N-phenyl carbamic acid ester as a starting material has a high solubility in aqueous inorganic acid solutions, the resultant diphenylmethane dicarbamic acid diester has a lower solubility, thus presenting a large difference in solubility between them. As a result, the resultant compound is precipitated outside the reaction system. However, if a nondissolved N-phenyl carbamic acid is present, it is suspended in the aqueous phase. The resultant diphenylmethane dicarbaminc acid diester tends to be dissolved in this suspension and may react therewith. For this reason, the reaction progresses while the N-phenyl carbamic acid ester is completely dissolved in the aqueous phase.

The methylating agent is formaldehyde or a material for generating formaldehyde under the reaction conditions of the present invention. Typical examples of the methylating agent are an aqueous formaldehyde solution, paraformaldehyde, trioxane, methylal, and other formals. These methylating agents are preferably in the form of either a homogeneous aqueous solution or a homogeneous aqueous acid solution, when added to the reaction system. Among the methylating agents, the formaldehyde solution is normally used. The content of formaldehyde falls within the range of an equivalent amount of 0.5 to 10 with respect to the N-phenyl carbamic acid ester.

The reaction temperature is preferably 20° C. to 150° C. and more preferably 50° C. to 120° C. If the reaction temperature is excessively low, the reaction is retarded. However, if the reaction temperature is excessively high, a side reaction such as hydrolysis is undesirably effected.

A reaction pressure is the pressure naturally obtained at the reaction temperature.

The reaction time varies according to the concentration of the N-phenyl carbamic acid ester material, the type and concentration of the acid, and the reaction temperature. The reaction time is normaly 10 minutes to 5 hours, in the batch process.

The reaction method is not limited to a specific method; however, the batch method can be used as a simple reaction method. According to this method, the material N-phenyl carbamic acid ester as the starting material is dissolved in an aqueous acid solution. The methylating agent is added dropwise under stirring, to enable the reaction to proceed while the reaction temperature is maintained. Diphenylmethane dicarbamic acid diester crystals precipitated after the reaction are filtered and washed with water, so as to remove the acid therefrom. The washed crystals are then dried.

In order to further improve the effect of the present invention, an aqueous acid solution and an N-phenyl carbamic acid ester are mixed by mixer 1. The resultant mixture is supplied to reaction chamber 2, where a methylating agent is added to it. The mixture with the methylating agent is supplied to filter 3, to separate and recover a diphenylmethane dicarbamic acid diester. At the same time, the used aqueous acid solution is returned to mixer 1. According to this method, the resultant diphenylmethane dicarbamic acid diester is not left in reaction chamber 2 for a long period of time and can be continuously filtered and separated. Therefore, the side reaction of the diphenylmethane dicarbamic diester can be further prevented.

According to the present invention, the difference in solubility between the N-phenyl carbamic acid ester as a starting material and the diphenylmethane dicarbamic acid diester as a final compound is utilized to cause the reaction to proceed while the N-phenyl carbamic acid ester is being completely dissolved. Therefore, the resultant compound can be precipitated outside the reaction system, to prevent it from reacting with the nonreacted N-phenyl carbamic acid ester. For this reason, the diphenylmethane dicarbamic acid diester can be manufactured at a high selectivity rate.

Furthermore, since the diphenylmethane dicarbamic acid diester as the final compound is crystallized in the reaction chamber, it can be easily separated from the reaction solution, by filtering.

Moreover, the aqueous acid solution can be reused after the diphenylmethane dicarbamic acid diester is separated from the reaction solution.

EXAMPLES

The present invention will now be described in detail by way of examples.

EXAMPLE 1

350 g of 18 wt % hydrochloric acid and 4.70 g of N-phenyl carbamic acid methyl were poured into a glass flask having an inner volume of 500 ml. The hydrochloric acid and the N-phenyl carbamic acid methyl were stirred by an electromagnetic stirrer and heated to 100° C. In this state, the N-phenyl carbamic acid methyl was completely dissolved in the hydrochloric acid solution. While the temperature was maintained at 100° C., 4.00 g of a 35% aqueous formaldehyde solution were added dropwise to the heated solution. Thereafter, the reaction was continued under stirring for 60 minutes. The resultant solution was then cooled to room temperature, and the precipitated white solid particles were separated by filtering. The white solid particles were washed with water a few times, to remove the acid therefrom. The white solid particles were dried in a vacuum and weighed, their weight being 4.42 g. The white solid particles were analyzed by high-speed liquid chromatography and were found to contain 2% of N-phenyl carbamic acid methyl and 98% of diphenylmethane dicarbamic acid dimethyl ester. No compounds having three or more nuclei were detected. The yield of diphenylmethane dicarbamic acid methyl was 89%.

After the diphenylmethane dicarbamic acid dimethyl ester was removed, 4.70 g of N phenyl carbamic acid methyl were dissolved in the resultant aqueous acid solution as a filtered solution, and 1.30 g of a 35% aqueous formaldehyde solution were added dropwise to the solution. The resultant solution was subjected to reaction at a temperature of 100° C. for 60 minutes. The resultant compound was weighed, its weight being 4.30 g, and was found to contain 97% of diphenylmethane dicarbamic acid dimethyl ester.

EXAMPLES 2 to 4

Following the same procedures as in Example 1, N-phenyl carbamic acid ester was reacted to obtain diphenylmethane dicarbamic acid ester. The reaction conditions and results are summarized in Table 1 below.

TABLE 1

| | N—Phenyl Carbamic Acid Ester | | Aqueous Solution of Acid | | |
|---|---|---|---|---|---|
| | Material Name | Weight (g) | Material Name | Concentration (wt %) | Weight (g) |
| Example 2 | PhNHCOOMe | 4.70 | Hydrochloric Acid | 18 | 400 |
| Example 3 | PhNHCOOEt | 1.75 | Hydrochloric Acid | 18 | 350 |
| Example 4 | PhNHCOOMe | 2.17 | Sulfuric Acid | 25 | 260 |

| | Methylating Agent | | Temperature (°C.) | Reaction Time (min) | Product Weight (g) | Yield (%) |
|---|---|---|---|---|---|---|
| | Agent Name | Weight (g) | | | | |
| Example 2 | Aqueous Solution of Formaldehyde (35%) | 2.60 | 100 | 60 | 3.76 | 75 |
| Example 3 | Aqueous Solution of Formaldehyde (35%) | 1.00 | 100 | 60 | 1.44 | 75 |
| Example 4 | Aqueous Solution of Formaldehyde (35%) | 1.86 | 100 | 60 | 1.65 | 72 |

COMPARATIVE EXAMPLE 300 g of 24 wt % hydrochloric acid and 100 g of N-phenyl carbamic acid ethyl were poured into a glass flask having an inner volume of 500 ml. The hydrochloric acid and the N-phenyl carbamic acid ethyl were stirred by an electromagnetic stirrer and heated to 100° C. In this state, the N-phenyl carbamic acid ethyl ester was in an emulsified state in the hydrochloric acid solution. While the temperature was maintained at 100° C., 26 g of a 35% aqueous formaldehyde solution were added dropwise to the heated solution. Thereafter, the reaction was continued under stirring for 5 hours. The resultant solution was then cooled to room temperature, and the precipitated organic layer was separated by filtering. The white solid particles were washed with water to remove the acid therefrom. The white solid particles were dried and weighed, their weight being 94 g. The white solid particles were analyzed by high-speed liquid chromatography and were found to contain 15% of N-phenyl carbamic acid ethyl and 46% of diphenylmethane dicarbamic acid ethyl. Of the compounds detected, 23% were found to have three or more nuclei. The yield of diphenylmethyl dicarbamic acid ethyl was 42% and the selectivity rate was 49%.

What is claimed is:

1. A method of producing a diphenylmethane dicarbamic acid diester with a recovery of at least 72%, comprising reacting an N-phenyl carbamic acid ester with a methylating agent in an aqueous inorganic acid solution to form said diphenyldicarbamic acid diester and, during the reaction preventing the formation of a suspension of N-phenylcarbamic acid ester in the mixture by maintaining the concentration of N-phenylcarbamic acid ester at not more than the solubility thereof at the reaction temperature.

2. A method according to claim 1 wherein the given aqueous inorganic acid solution is such that a ratio of the solubility of the N-phenyl carbamic acid ester as a starting material to the solubility of the diphenylmethane dicarbamic acid diester as a product is not more than 0.1.

3. A method according to claim 1 wherein the concentration of the aqueous inorganic acid solution is 1 to 80% by weight.

4. A method according to claim 1 wherein the reaction temperature falls within a range of 20° C. to 150° C.

5. A method according to claim 1 wherein the reaction temperature falls wtihin a range of 50° C. to 120° C.

6. The method of claim 1 wherein,
   in the aqueous inorganic acid solution, the ratio of the solubility of the N-phenyl carbamic acid ester as a starting material to the solubility of the diphenylmethane dicarbamic acid ester as a product is not more than 0.1;
   the concentration of the aqueous inorganic acid solution is 1 to 80% by weight; and
   the reaction temperature falls within a range of 20° C. to 150° C.

7. The method of claim 6 wherein the aqueous inorganic acid solution contains hydrochloric or sulphuric acid as the inorganic acid; the N-phenyl carbamic acid ester is

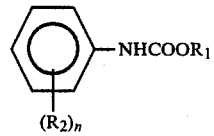

(I)

wherein $R_1$ is an alkyl, an alicylic or an aromatic group; each $R_2$ is individually selected from hydrogen, alkyl, halogen, nitro or alkoxyl and n is 0 to 4.

8. The method of claim 6 wherein the N-phenyl carbamic acid ester is selected from the group consisting of N-phenyl carbamic acid methyl, N-phenyl carbamic acid ethyl, N-phenyl carbamic acid n-propyl, N-phenyl carbamic acid isopropyl, N-phenyl carbamic acid phenyl, N-phenyl carbamic acid cyclohexyl, N-o-chlorophenyl carbamic acid methyl, N-m-chlorophenyl carbamic acid methyl, N-o-methylphenyl carbamic acid methyl, N-m-methyl carbamic acid methyl, N-2,6-dimethyl carbamic acid methyl, N-o-nitrophenyl carbamic acid methyl, and N-o-methoxy carbamic acid methyl.

9. The method of claim 8 wherein the methylating agent is formaldehyde, or a material for generating formaldehyde under reaction conditions of the method, used in an equivalent amount of 0.5 to 10 with respect to the N-phenyl carbamic acid ester.

10. The method of claim 6 wherein the N-phenyl carbamic acid ester is PhNHCOOMe or PhNHCOOEt.

11. The method of claim 1 wherein the N-phenyl carbamic acid ester is PhNHCOOMe or PhNHCOOEt.

* * * * *